United States Patent [19]
Bader

[11] Patent Number: 5,948,655
[45] Date of Patent: *Sep. 7, 1999

[54] METHOD OF APPLYING HEPATOCYTES TO HOLLOW FIBERS

[76] Inventor: Augustinus Bader, Hinter den langen Hoefen 16, D-31275 Lehrte, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/578,556

[22] PCT Filed: Jul. 6, 1994

[86] PCT No.: PCT/EP94/02217

§ 371 Date: Mar. 6, 1996

§ 102(e) Date: Mar. 6, 1996

[87] PCT Pub. No.: WO95/02037

PCT Pub. Date: Jan. 19, 1995

[30] Foreign Application Priority Data

Jul. 8, 1993 [DE] Germany ............................... 43 22 746

[51] Int. Cl.$^6$ .............................. C12N 11/02; C12N 5/00; C12N 5/06; C12M 3/00
[52] U.S. Cl. .......................... 435/177; 435/174; 435/180; 435/182; 435/395; 435/400; 435/289.1; 435/297.1; 435/297.4
[58] Field of Search ...................................... 435/174, 176, 435/177, 178, 180, 182, 289.1, 293.1, 297.1, 297.4, 395, 400

[56] References Cited

U.S. PATENT DOCUMENTS 5,605,835 2/1997 Hu et al. ............................... 435/297.2
5,658,797 8/1997 Bader ................................... 435/284.1

FOREIGN PATENT DOCUMENTS

WOA89 01967 3/1989 WIPO .
WOA93 18133 9/1993 WIPO .

OTHER PUBLICATIONS

Patent Abstracts of Japan–13 vol. 14, No. 254 (C–0724), May 31, 1990.

Nyberg et al., Bilirubin Conjucation in a Three Compartment Hollow Fiber Bioreactor, Proceedings of the 12th Annual International Conference of the IEEE Engineering in Medicine and Biology Society, vol. 12: Part 1/5, Pederson et al., Eds., pp. 443–444, Nov. 1–4, 1990.

*Primary Examiner*—David M. Naff
*Attorney, Agent, or Firm*—Welsh & Katz, Ltd.

[57] ABSTRACT

Cells such as hepatocytes are applied to hollow fibers by forming a first gelled matrix layer on the outside surface of the fibers, adhering cells to the matrix layer and forming a second gelled matrix layer covering the adhered cells. To form the matrix layers, a liquid matrix-forming material such as containing collagen is applied and then gelled. An acidic liquid matrix-forming material may be used to prepare the second matrix layer. The hollow fibers may be cooled to less than 15° C. before forming the first gelled matrix layer. Three-dimensional co-cultures may be formed by applying non-parenchyma cells to the inside of the walls of the hollow fibers.

5 Claims, 1 Drawing Sheet

METHOD OF APPLYING HEPATOCYTES TO HOLLOW FIBERS

FIELD OF THE INVENTION

The invention relates to a process for treating cell cultures, in particular hepatocytes on hollow fibres, which are at least partially gas and/or liquid permeable, whereby the cell cultures are applied on or into the hollow fibres and suspension medium is conveyed as a culture medium through or around the hollow fibres. The invention also relates to a device for performing the process.

BACKGROUND OF THE INVENTION

In medicine and in pharmacognosy it is frequently necessary to perform experiments with cell cultures, in particular with liver cells (hepatocytes). This applies, for example, to their culture, their observation, in particular the observation of reactions on foreign and/or poisonous substances, to storage and the like.

Furthermore the quest for suitable organ replacement is becoming increasingly important.

In known systems for the culture of liver cells in so-called hollow fibre reactors, the cells were previously introduced in liquid form either inside or outside the hollow fibres by suspension in a solution, such as, e.g. a culture medium. After the adhesion of these cells to the fibres or also by leaving non-adherent cells in the interspaces between the adhered cells in the form of an aggregate formation, the system was used for the respective purpose.

The crucial disadvantage of the known processes is that intercellular contacts between the individual hepatocytes are only developed in an inadequate manner or in some cases not at all.

The loss of cellular morphology not only entails a loss of function, but also prevents regenerative power after a stimulation of the cells with growth factors in a longer-term culture system. Longer-term cultivation would however be of great significance with the use of human hepatocytes, as they are not available in any quantity.

SUMMARY OF THE INVENTION

The object of the present invention is to create a process of the type mentioned at the beginning with which a mass culture is possible, whereby one wishes to achieve, as far as possible, an "in vivo" state, in particular the longest possible life-span.

This object is achieved in accordance with the invention in that the cells of the cell cultures are covered with an outer matrix layer on the side faced away from the hollow fibres after their application and adhesion to the hollow fibres, directly or indirectly over a first matrix layer.

With the process in accordance with the invention, the cell cultures are embedded in an extra-cellular matrix layer in the manner of a sandwich technique known per se. At the same time a reorganisation of the cell shape and a renewed formation of microvilli on the side or sides faced towards the matrix surfaces occur. This corresponds to the natural shape of the liver cells and promotes exchange of substances in the manner of sinusoidal membranes. However, apart from these morphological advantages, the functional preservation of these cells is also important.

One of the most important features of the invention is consequently represented by the second, i.e. the outer, matrix layer, which envelops the cell cultures. This enveloping is however only performed when the cell cultures are applied to the hollow fibres and have adhered there. This can occur directly or over an intermediate first matrix layer. The use of a first matrix layer depends on what type of cell cultures are to be treated and what material is used for the hollow fibres. In connection with hollow fibres, specific cell cultures require no separate matrix layers as an intermediate layer, but can adhere directly to the surfaces of specific hollow fibres.

In an advantageous embodiment of the invention it may be specified that the cells are applied to a plurality of hollow fibres on their outer side in each case, with the cells being covered on the outside by the matrix layer in each case.

Depending on the diameter of the hollow fibres, the cell cultures and the matrix layer or respectively the matrix layers may also be synthesised internally in the cavities of the hollow fibres. However for practical reasons the suspension or culture medium is preferably introduced inwardly through the hollow fibres and made to pass outwardly thorough the walls of the hollow fibres to supply the cell cultures.

To prevent a premature gelling of collagen, which is generally present in the matrix layer as the main constituent, the hollow fibres are cooled for the application of the first matrix layer to temperatures of less than 15° C., preferably less than 4° C.

The cell cultures may be applied in an advantageous manner over a substrate in the form of a suspension medium, with the suspension medium flowing away after the application of the cell cultures to the hollow fibres.

Corresponding free locations, into which the second matrix layer can flow during the application of said layer, are produced by the suspension medium flowing away. In this manner it is ensured that the cells are adhered or activated in bipolar manner. As a result they are both intact and functionally more stable from the morphological point of view in the same way as in nature.

In a very advantageous embodiment of the invention it may be specified that to create three-dimensional co-cultures with the cell culture to be treated, non-parenchyma cells are applied to the side faced towards the influx of culture medium.

The non-parenchyma cells are generally applied to the hollow fibres by conventional introduction in liquid suspension before the application of the first matrix layer.

Alternatively to this, the non-parenchyma cells may however be applied inside the hollow fibres to their inner walls, as a result of which interactions with the cells which have adhered in bipolar fashion and are located on the outside of the hollow fibres are also possible. The cells which have adhered in bipolar fashion, e.g. hepatocytes, are in this manner surrounded by a screen of non-parenchyma cells outside the matrix layers. The non-parenchyma cells in practice act as a barrier. They can filter out and modify certain substances and also react on substances before these substances encounter the hepatic cells.

BRIEF DESCRIPTION OF THE DRAWINGS

An exemplified embodiment of the invention is represented in principle below by means of the drawings.

DETAILED DESCRIPTION OF THE INVENTION

Figure 1:
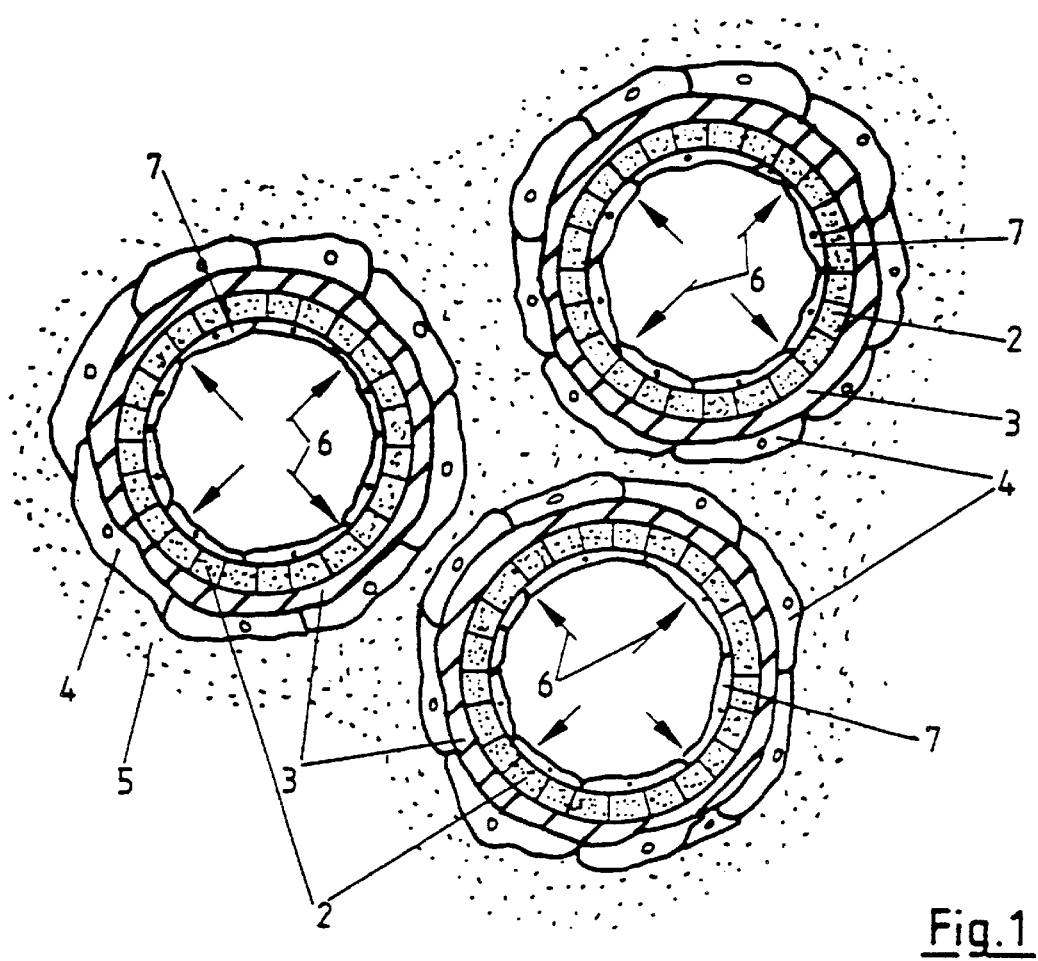
FIG. 1 shows an enlarged representation of three hollow fibres with hepatocytes and matrix layers and also with non-parenchyma cells.
Figure 2:
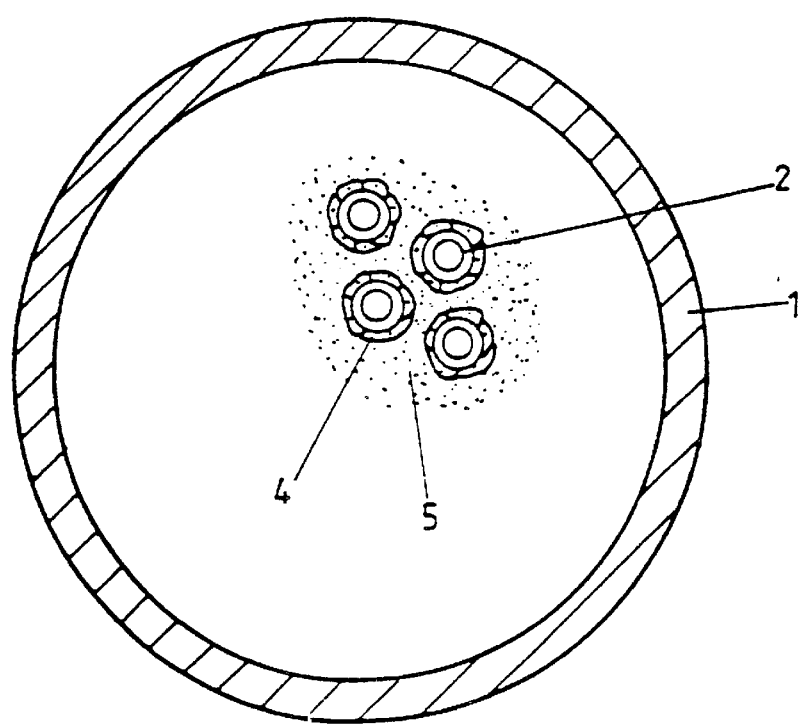
FIG. 2 shows a cross section through a device in the form of a reactor with hollow fibres disposed therein (only partially represented).

A plurality of hollow fibres 2 are disposed next to one another in a hollow fibre reactor, which may be constructed as a tubular reactor or receptacle 1. The hollow fibres may be made from porous polypropylene or polysulfone. However naturally other materials are also possible. The only essential factor is that an exchange of substances through the walls of the hollow fibres is possible by virtue of an appropriate porosity. The hollow fibres and consequently also the receptacle itself may have an effective length of 20 to 25 cm, however the length is also only given by way of example.

A first matrix layer 3 is applied to the outside of these hollow fibres in each case. For this purpose the hollow fibres 2 are cooled, and namely for the introduction of the matrix layer, which consists of a type 1 collagen, for example, with it also being possible to add laminins, proteins or other organic substances. This takes place in liquid form, with cooling being performed to 4° C. to prevent premature gelling.

If the first matrix layer 3 is applied to the outside, an internal diameter of the hollow fibres of 0.1 mm, for example, will generally suffice. If the synthesis with the cell culture to be treated is to occur internally, larger diameters, for example 1, 2, 3 mm or more, will generally be required.

The first matrix layer 3 serves as a coating layer for the hollow fibres in order to assist an adhesion of the cells 4 of the cell culture to be treated. With an appropriate choice of material for the hollow fibres 2 and a cell culture harmonising therewith, the first matrix layer 3 may also be omitted where appropriate.

In a second step the cells 4 of the cell culture are introduced in suspension form into the reactor 1. With the introduction into the space outside the hollow fibres 2, a flowing away of the suspension medium into the interior of the hollow fibres 2 occurs, whereby the cells 4 remain in the space outside the hollow fibres 2 previously coated with the first matrix layer 3 on said matrix layer. The actual spatial requirement of the cells 4 is consequently reduced by the percentage of volume of the suspension medium which has flowed away.

Then one should preferably wait at least one to two hours to give the cells 4 the possibility of adhering to the first matrix layer 3 and for the formation of microvilli, so that intercellular contacts can be created without interference. At the same time the formation of bile canaliculi occurs at the intercellular contact points in the region of the apical cell membrane sides of the cells 4. Hepatocytes are used as cells 4 in the exemplified embodiment.

In a third step a separate second matrix layer 5 is introduced into the reactor. For this a matrix mixture at preferably 4° C. in an acid solution is mixed with a basic medium concentrate in the ratio 1:10 and is then introduced in liquid form into the reactor 1. With the medium concentrate it concerns concentrated culture medium which is gelled by the concentration.

Introduction is made into the spaces becoming free by the suspension medium flowing away, whereby the interspaces between the hollow fibres 2 are generally filled on the outside. In practice this means that the second matrix layer 5 is only introduced if there is a structured form of the already adhered cells 4.

The cells 4 are completely enveloped on the outside by the second matrix layer 5. In this manner they can be attached both on the inside and also on the outside, i.e. in bipolar fashion. Consequently a three-dimensional structure is produced, with the cells having developed intercellular contact in the same way as in nature and interacting in a corresponding manner.

With the onset of heating and a change in pH, after the introduction of the second matrix layer 5 a hardening of this matrix layer occurs, whereby internal contact with the cell membrane surfaces is formed. By the coating and the enveloping, the cells 4 can in this manner develop microvilli on the cell membrane side faced towards the second outer matrix layer 5, the sinusoidal side, also in a mass cultivable system with the plurality of hollow fibres 2.

If this second matrix layer 2 were not present, the morphological disadvantage resulting therefrom would lead to a continuous functional loss of the cells. The possibility of a migration and propagation of the cells 4 inside the two matrix layers, such as, for example, in response to proliferation stimuli, is possible.

Growth factors are provided to exploit the proliferation and regenerative power of the hepatic cells which have adhered in bipolar fashion in accordance with the invention.

Culture medium, such as, e.g. blood, plasma, proteins and/or an oxygen-containing nutrient medium for supplying the cells 4, is introduced from one end side of the cylindrical reactor 1 into the interior of the hollow fibres 2, whereby it passes in the direction of the arrows 6 through the walls of the hollow fibres 2 from the inside to the outside by virtue of their porous character. Similarly, an exchange of substances from the outside to the inside is also possible. Residual culture medium flows away again at the other end side of the receptacle 1.

In order to create three-dimensional co-cultures, non-parenchyma cells 7 can be applied to the inner walls of the hollow fibres 2 in each case. Instead of an application on the inside of the hollow fibres, they may also be applied to the outside of the hollow fibres 2, if said fibres are introduced before the first matrix layer 3. By virtue of the porosity of the hollow fibres 2, interactions with the cells 4 located outside the hollow fibres 2 may however occur even when arranged on the inner sides of the hollow fibres 2.

Endothelial cells, Kupffer's cells, ito cells and pit cells, for example, may be provided as non-parenchyma cells 7.

I claim:

1. A process for treating hepatocyte cell cultures on hollow permeable fibers, said hollow fibers having an interior surface and an exterior surface including the steps of:

forming a first matrix layer on the outside of said hollow fibers by applying a liquid matrix-forming material to the outside of said hollow fibers and gelling said matrix-forming material;

contacting a suspension of cells with said first matrix layer for adherence of said cells thereto;

forming a second matrix layer on said adhered cells by contacting said adhered cells with said liquid matrix-forming material and gelling said matrix-forming material to cover said adhered cells.

2. A process according to claim 1, further including the step of cooling said hollow fibers prior to applying said liquid matrix-forming material to temperatures of less than 15° C.

3. A process according to claim 1, wherein said liquid matrix-forming material is acidic that is used to form said second matrix layer.

4. A process according to claim 1, further including the step of forming three-dimensional co-cultures with, non-parenchyma cells by first applying said non-parenchyma cells to the inside of the walls of the hollow fibers.

5. A process according to claim 1, wherein the matrix layers comprise collagen.

* * * * *